United States Patent
Yamanaka et al.

(10) Patent No.: US 8,859,655 B2
(45) Date of Patent: *Oct. 14, 2014

(54) FLAME RETARDANT RESIN COMPOSITION AND MOLDED ARTICLE THEREOF

(75) Inventors: Katsuhiro Yamanaka, Chiyoda-ku (JP); Fumitaka Kondo, Chiyoda-ku (JP)

(73) Assignee: Teijin Chemicals, Ltd., Tokyo (JP)

( * ) Notice: Subject to any disclaimer, the term of this patent is extended or adjusted under 35 U.S.C. 154(b) by 294 days.

This patent is subject to a terminal disclaimer.

(21) Appl. No.: 13/201,929

(22) PCT Filed: Feb. 12, 2010

(86) PCT No.: PCT/JP2010/052484
§ 371 (c)(1),
(2), (4) Date: Aug. 17, 2011

(87) PCT Pub. No.: WO2010/095699
PCT Pub. Date: Aug. 26, 2010

(65) Prior Publication Data
US 2011/0301266 A1    Dec. 8, 2011

(30) Foreign Application Priority Data

Feb. 19, 2009  (JP) ................. 2009-036535
Feb. 19, 2009  (JP) ................. 2009-036536

(51) Int. Cl.
| | |
|---|---|
| C08K 5/5357 | (2006.01) |
| C09K 21/12 | (2006.01) |
| C08L 67/04 | (2006.01) |
| C07F 9/6571 | (2006.01) |
| C08L 51/04 | (2006.01) |
| C08L 25/12 | (2006.01) |
| C08L 55/02 | (2006.01) |
| C08L 69/00 | (2006.01) |

(52) U.S. Cl.
CPC ............. *C09K 21/12* (2013.01); *C08K 5/5357* (2013.01); *C08L 51/04* (2013.01); *C08L 67/04* (2013.01); *C07F 9/657181* (2013.01); *C08L 25/12* (2013.01); *C08L 55/02* (2013.01); *C08L 69/00* (2013.01)
USPC .......................................................... 524/120

(58) Field of Classification Search
USPC ........................................................ 524/120
See application file for complete search history.

(56) References Cited

U.S. PATENT DOCUMENTS

| | | | |
|---|---|---|---|
| 2004/0127611 A1* | 7/2004 | Yamanaka et al. ............ | 524/116 |
| 2005/0272875 A1 | 12/2005 | Desbois et al. | |
| 2007/0142503 A1 | 6/2007 | Yamada et al. | |
| 2008/0097008 A2 | 4/2008 | Yamada et al. | |

FOREIGN PATENT DOCUMENTS

| | | | |
|---|---|---|---|
| JP | 2001-164014 | | 6/2001 |
| JP | 2004-018764 | | 1/2004 |
| JP | 2004-018765 | | 1/2004 |
| JP | 2004-018766 | | 1/2004 |
| JP | 2004-018767 | | 1/2004 |
| JP | 2004-277552 | | 10/2004 |
| JP | 2005-023260 | | 1/2005 |
| JP | 2005-048067 | * | 2/2005 |
| JP | 2005-139431 | | 6/2005 |
| JP | 2005-139441 | | 6/2005 |
| JP | 2005-264086 | * | 9/2005 |
| JP | 2005-538239 | | 12/2005 |
| JP | 2006-016558 | | 1/2006 |
| JP | 2007-246730 | | 9/2007 |
| JP | 2008-019294 | | 1/2008 |
| JP | 2008-156616 | | 7/2008 |
| WO | 2008/026575 | | 3/2008 |
| WO | 2009/145341 | | 12/2009 |

OTHER PUBLICATIONS

Machine translation of Saito (2005).*
Machine translation of Hironaka (2005).*
International Search Report mailed Apr. 27, 2010 in International (PCT) Application No. PCT/JP2010/052484.
International Preliminary Report on Patentability and Written Opinion mailed Sep. 22, 2011 in International (PCT) Application No. PCT/JP2010/052484.
Japanese Office Action issued Jun. 18, 2014 in corresponding Japanese Patent Application No. 2011-500652.

* cited by examiner

*Primary Examiner* — Doris Lee
(74) *Attorney, Agent, or Firm* — Wenderoth, Lind & Ponack, LLP

(57) ABSTRACT

A flame retardant resin composition which has high flame retardancy, excellent heat resistance and physical properties and is obtained from a plant-derived raw material and a molded article thereof.

The flame retardant resin composition comprises:
(A) 100 parts by weight of a polylactic acid and/or a lactic acid copolymer (component A);
(B) 1 to 100 parts by weight of a styrene-based resin and/or a polycarbonate resin (component B); and
(C) 1 to 100 parts by weight of an organic phosphorus compound represented by the following formula (1) (component C).

$$\begin{array}{c} O-CH_2 \quad CH_2-O \\ O=P \diagdown \diagup C \diagdown \diagup P=O \\ X^1 \diagup \diagdown O-CH_2 \quad CH_2-O \diagdown X^2 \end{array} \quad (1)$$

(wherein $X^1$ and $X^2$ are the same or different and each an aromatic substituted alkyl group represented by the following formula (2))

$$AL Ar_n \quad (2)$$

(wherein AL is a branched or linear aliphatic hydrocarbon group having 1 to 5 carbon atoms, Ar is a phenyl group, naphthyl group or anthryl group all of which may have a substituent. n is an integer of 1 to 3, and Ar can be bonded to any carbon atom contained in AL.).

18 Claims, No Drawings

FLAME RETARDANT RESIN COMPOSITION AND MOLDED ARTICLE THEREOF

TECHNICAL FIELD

The present invention relates to a flame retardant resin composition which is obtained from a plant-derived raw material and has high flame retardancy, high heat resistance and excellent physical properties and to a molded article thereof. More specifically, it relates to a substantially halogen-free flame retardant resin composition comprising a specific organic phosphorus compound and to a molded article thereof.

BACKGROUND ART

Resins such as polypropylenes (PP), acrylonitrile-butadiene-styrene (ABS), polyamides (PA6, PA66), polyesters (PET, PBT) and polycarbonates (PC) are generally used as raw materials for obtaining resin molded articles. These resins are produced from raw materials obtained from oil resources. In recent years, problems such as the depletion of oil resources and global environment have been apprehended, and the production of a resin from a raw material obtained from biogenic matter such as a plant has been desired. Especially when a global environmental problem is taken into consideration, a resin obtained from a plant-derived raw material is regarded as a resin with a low impact on the global environment from the concept "carbon neutral" which means that the balance of carbon is neutral in view of the amount of carbon dioxide absorbed during the growth of a plant even when it is burnt after use.

Meanwhile, to use a resin obtained from a plant-derived raw material as an industrial material, especially an electric/electronic-related part, OA-related part or auto part, flame retardancy must be provided to the resin from the viewpoint of safety.

Various attempts have been made for the flame retardation of resins obtained from plant-derived raw materials, especially polylactic acid resin, and a certain level of flame retardation has been achieved (Patent Documents 1 to 6). However, a large amount of a flame retardant is used to flame retard these resins, whereby the physical properties and heat resistance of the resins are impaired by the characteristic properties of the flame retardant.
(Patent Document 1) JP-A 2001-164014
(Patent Document 2) JP-A 2004-277552
(Patent Document 3) JP-A 2005-023260
(Patent Document 4) JP-A 2005-139441
(Patent Document 5) JP-A 2007-246730
(Patent Document 6) JP-A 2008-019294

DISCLOSURE OF THE INVENTION

It is a first object of the present invention to provide a flame retardant resin composition which is obtained from a plant-derived raw material and has high flame retardancy, high heat resistance and excellent physical properties and a molded article thereof.

It is a second object of the present invention to provide a substantially halogen-free flame retardant resin composition which comprises a specific organic phosphorus compound and a molded article thereof.

The inventors of the present invention have found that a resin composition having excellent flame retardancy and heat resistance is obtained when a specific organic phosphorus compound is contained in resin components such as polylactic acid obtained from biogenic matter and a styrene-based resin obtained from an oil resource.

That is, according to the present invention, there are provided:
1. A flame retardant resin composition comprising:
   (A) 100 parts by weight of a polylactic acid and/or a lactic acid copolymer (component A);
   (B) 1 to 100 parts by weight of a styrene-based resin and/or a polycarbonate resin (component B); and
   (C) 1 to 100 parts by weight of an organic phosphorus compound represented by the following formula (1).

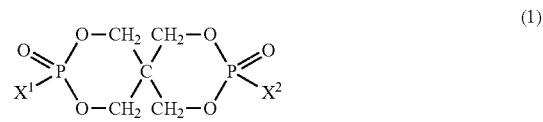

(wherein $X^1$ and $X^2$ are the same or different and each an aromatic substituted alkyl group represented by the following formula (2):

(wherein AL is a branched or linear aliphatic hydrocarbon group having 1 to 5 carbon atoms, Ar is a phenyl group, naphthyl group or anthryl group all of which may have a substituent. n is an integer of 1 to 3, and Ar can be bonded to any carbon atom contained in AL.)
2. The flame retardant resin composition in the above paragraph 1, wherein the organic phosphorus compound (component C) is at least one compound selected from the group consisting of organic phosphorus compounds represented by the following formulae (3) and (4).

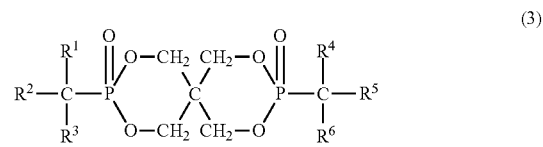

(wherein $R^2$ and $R^5$ may be the same or different and each a phenyl group, naphthyl group or anthryl group all of which may have a substituent. $R^1$, $R^3$, $R^4$ and $R^6$ may be the same or different and each a substituent selected from hydrogen atom, branched or linear alkyl group having 1 to 4 carbon atoms, and phenyl group, naphthyl group or anthryl group all of which may have a substituent.)

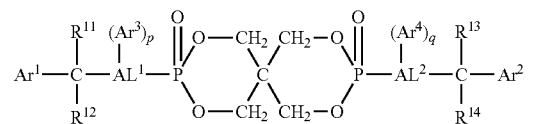

(wherein $Ar^1$ and $Ar^2$ may be the same or different and each a phenyl group, naphthyl group or anthryl group and may have a substituent in the aromatic ring, $R^{11}$, $R^{12}$, $R^{13}$ and $R^{14}$ may be the same or different and each a hydrogen atom, aliphatic hydrocarbon group having 1 to 3 carbon atoms, phenyl group, naphthyl group or anthryl group and may have a substituent in the aromatic ring. $AL^1$ and $AL^2$ may be the same or different and each a branched or linear aliphatic hydrocarbon group having 1 to 4 carbon atoms. Ar³ and Ar⁴ may be the same or different and each a phenyl group, naphthyl group or anthryl group and may have a substituent in the aromatic ring. p and q are each an integer of 0 to 3, and Ar³ and Ar⁴ can be bonded to any carbon atom in $AL^1$ and $AL^2$, respectively.)

3. The flame retardant resin composition in the above paragraph 1, wherein the organic phosphorus compound (component C) is represented by the following formula (5):

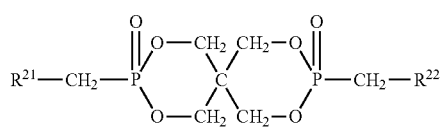

(5)

(wherein $R^{21}$ and $R^{22}$ are the same or different and each a phenyl group, naphthyl group or anthryl and may have a substituent in the aromatic ring.)

4. The flame retardant resin composition in the above paragraph 1, wherein the organic phosphorus compound (component C) is a compound represented by the following formula (1-a).

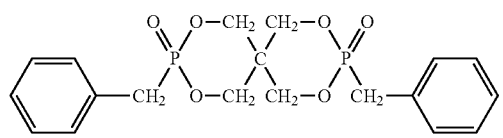

(1-a)

5. The flame retardant resin composition in the above paragraph 1, wherein the organic phosphorus compound (component C) is represented by the following formula (6).

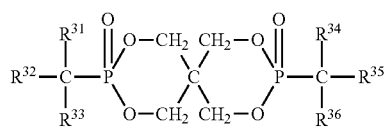

(6)

(wherein $R^{31}$ and $R^{34}$ may be the same or different and each a hydrogen atom or aliphatic hydrocarbon group having 1 to 3 carbon atoms. $R^{33}$ and $R^{36}$ may be the same or different and each an aliphatic hydrocarbon group having 1 to 4 carbon atoms. $R^{32}$ and $R^{35}$ may be the same or different and each a phenyl group, naphthyl group or anthryl group and may have a substituent in the aromatic ring.)

6. The flame retardant resin composition in the above paragraph 1, wherein the organic phosphorus compound (component C) is a compound represented by the following formula (1-b).

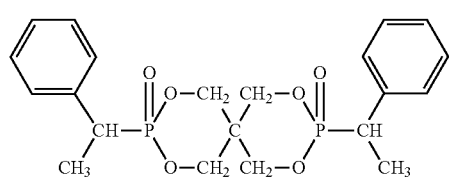

(1-b)

7. The flame retardant resin composition in the above paragraph 1, wherein the organic phosphorus compound (component C) is represented by the following formula (7).

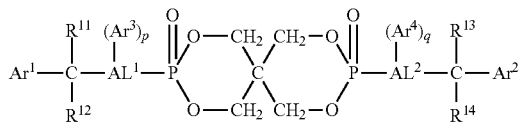

(7)

(wherein $Ar^1$ and $Ar^2$ may be the same or different and each a phenyl group, naphthyl group or anthryl group and may have a substituent in the aromatic ring. $R^{11}$, $R^{12}$, $R^{13}$ and $R^{14}$ may be the same or different and each a hydrogen atom, aliphatic hydrocarbon group having 1 to 3 carbon atoms, phenyl group, naphthyl group or anthryl group and may have a substituent in the aromatic ring. $AL^1$ and $AL^2$ may be the same or different and each a branched or linear aliphatic hydrocarbon group having 1 to 4 carbon atoms. Ar³ and Ar⁴ may be the same or different and each a phenyl group, naphthyl group or anthryl group and may have a substituent in the aromatic ring. p and q are each an integer of 0 to 3, and Ar³ and Ar⁴ can be bonded to any carbon atom in $AL^1$ and $AL^2$, respectively.)

8. The flame retardant resin composition in the above paragraph 1, wherein the organic phosphorus compound (component C) is a compound represented by the following formula (1-c).

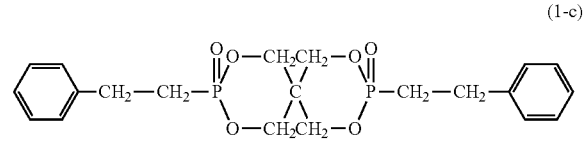 [SMILES: O=P1(CCc2ccccc2)OCC2(CO1)COP(=O)(CCc1ccccc1)OC2]

(1-c)

9. The flame retardant resin composition in the above paragraph 1, wherein the organic phosphorus compound (component C) is represented by the following formula (8).

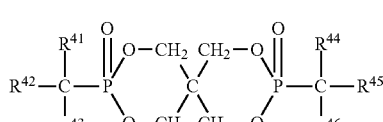

(8)

(wherein $R^{41}$ and $R^{44}$ may be the same or different and each a hydrogen atom, aliphatic hydrocarbon group having 1 to 4 carbon atoms, phenyl group, naphthyl group or anthryl group and may have a substituent in the aromatic ring, and $R^{42}$, $R^{43}$, $R^{45}$ and $R^{46}$ may be the same or different and each a phenyl group, naphthyl group or anthryl group and may have a substituent in the aromatic ring.)

10. The flame retardant resin composition in the above paragraph 1, wherein the organic phosphorus compound (component C) is a compound represented by the following formula (1-d).

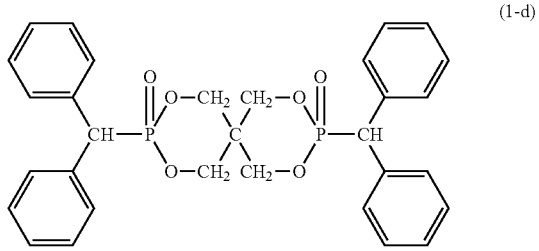 [SMILES: O=P1(C(c2ccccc2)c2ccccc2)OCC2(CO1)COP(=O)(C(c1ccccc1)c1ccccc1)OC2]

(1-d)

11. The flame retardant resin composition in the above paragraph 1, wherein the acid value of the organic phosphorus compound (component C) is not more than 0.7 mgKOH/g.
12. The flame retardant resin composition in the above paragraph 1 which achieves at least V-2 rating according to the UL-94 flame retardancy standard.
13. The flame retardant resin composition in the above paragraph 1, wherein the styrene-based resin (component B) has an MVR value at 200° C. under a load of 5 kg of 1 to 100 cm$^3$/10 min.
14. The flame retardant resin composition in the above paragraph 1, wherein the styrene-based resin (component B) has an MVR value at 220° C. under a load of 10 kg of 1 to 100 cm$^3$/10 min.
15. The flame retardant resin composition in claim 1, wherein the polycarbonate resin (component B) has an MVR value at 300° C. under a load of 1.2 kg of 0.1 to 80 cm$^3$/10 min.
16. The flame retardant resin composition in claim 1, wherein the polycarbonate resin (component B) has a content of the OH group existent at the terminal of not more than 100 eq/ton.
17. The flame retardant resin composition in the above paragraph 1 which has an HDT retention measured under a load of 0.45 MPa of not less than 95%.
18. A molded article formed from the flame retardant resin composition of the above paragraph 1.

According to the present invention, a flame retardant resin composition which is produced from a plant-derived raw material and has high flame retardancy is obtained without impairing the characteristic properties of resins.

BEST MODE FOR CARRYING OUT THE INVENTION

The flame retardant resin composition of the present invention will be described in more detail hereinunder.
(Polylactic Acid And/Or Lactic Acid Copolymer: Component A)

In the present invention, the polylactic acid is a polymer obtained from L-lactic acid, D-lactic acid, DL-lactic acid or a mixture thereof, or L-lactide which is a cyclic dimer of L-lactic acid, D-lactide which is a cyclic dimer of D-lactic acid, meso-lactide which is a cyclic dimer of L-lactic acid and D-lactic acid or a mixture thereof.

The method of producing the polylactic acid is not particularly limited but a generally known melt polymerization method may be used alone or in combination with a solid-phase polymerization method to produce the polylactic acid. Examples of the method are disclosed by U.S. Pat. Nos. 1,995,970, 2,362,511 and 2,683,136, and the polylactic acid is synthesized from a cyclic dimer of lactic acid which is generally called "lactide" by ring-opening polymerization. U.S. Pat. No. 2,758,987 discloses a ring-opening polymerization method in which a cyclic dimer of lactic acid (lactide) is melt polymerized.

In the present invention, the lactic acid copolymer is a copolymer obtained mainly from a lactic acid, as exemplified by a lactic acid-hydroxycarboxylic acid copolymer and a lactic acid-aliphatic polyhydric alcohol-aliphatic polybasic acid copolymer.

Examples of the hydroxycarboxylic acid used in the lactic acid copolymer used in the present invention include glycolic acid, 3-hydroxybutyric acid, 4-hydroxybutyric acid, 4-hydroxy valeric acid, 5-hydroxyvaleric acid, 4-hydroxyvaleric acid and 6-hydroxycaproic acid. They may be used alone or in combination of two or more. A cyclic ester intermediate of hydroxycarboxylic acid such as glycolide which is a dimer of glycolic acid or ε-caprolactone which is a cyclic ester of 6-hydroxycarproic acid may also be used.

Examples of the aliphatic polyhydric alcohol include aliphatic diols such as ethylene glycol, diethylene glycol, triethylene glycol, polyethylene glycol, propylene glycol, dipropylene glycol, 1,3-butanediol, 1,4-butanediol, 3-methyl-1,5-pentanediol, 1,6-hexanediol, 1,9-nonanediol, neopentyl glycol, decamethylene glycol and 1,4-cyclohexane dimethanol. They may be used alone or in combination of two or more.

Examples of the aliphatic polybasic acid include aliphatic dibasic acids such as succinic acid, oxalic acid, malonic acid, glutaric acid, adipic acid, pimelic acid, suberic acid, azelaic acid, sebacic acid, undecanedioic acid and dodecanedioic acid. They may be used alone or in combination of two or more.

The copolymer of lactic acid and hydroxycarboxylic acid is generally synthesized by the ring-opening polymerization of a cyclic ester intermediate of lactide and hydroxycarboxylic acid, and its production method is disclosed by U.S. Pat. Nos. 3,635,956 and 3,797,499. U.S. Pat. No. 5,310,865 discloses a method in which a mixture of lactic acid and hydroxycarboxylic acid is used as a raw material to carry out dehydration polycondensation directly. U.S. Pat. No. 4,057,537 discloses a ring-opening polymerization method in which lactic acid and a cyclic dimer of an aliphatic hydroxycarboxylic acid, for example, lactide and glycolide, and ε-caprolactone are melt polymerized in the presence of a catalyst. To produce a lactic acid copolymer directly by dehydration polycondensation and not ring-opening polymerization, a polylactic acid copolymer having a degree of polymerization suitable for use in the present invention is obtained by carrying out the azeotropic dehydration condensation of a lactic acid and optionally another hydroxycarboxylic acid preferably in the presence of an organic solvent, especially a phenyl ether-based solvent and removing water from the solvent distilled out particularly preferably by azeotropy to return a substantially anhydrous solvent into a reaction system.

U.S. Pat. No. 5,428,126 discloses a method in which a mixture of lactic acid, an aliphatic dihydric alcohol and an aliphatic dibasic acid is directly dehydrated and condensed. European Patent No. 0712880A2 discloses a method in which a polymer of polylactic acid, an aliphatic dihydric alcohol and an aliphatic dibasic acid is condensed in the presence of an organic solvent.

In the present invention, a suitable molecular weight control agent, branching agent and modifier may be added in the production of the polylactic acid or the lactic acid copolymer.

Polylactic acid which is a polymer of only a lactic acid is preferably used in the present invention, and a poly-L-lactic acid resin which is obtained mainly from L-lactic acid is particularly preferred. In general, L-lactic acid contains D-lactic acid which is an optical isomer, and its content is preferably not more than 15 wt %, more preferably not more than 10 wt %, particularly preferably not more than 5 wt %.

When a large amount of the optical isomer is contained, the crystallinity of the polylactic acid is reduced with the result that the obtained polylactic acid becomes softer. Although it is advantageously used in a molded article which is desired to be soft, it is not preferred for a composition which requires heat resistance.

(Styrene-Based Resin: Component B)

The styrene-based resin as the component B is selected from a homopolymer or copolymer of an aromatic vinyl monomer such as styrene, α-methylstyrene or vinyl toluene, and a copolymer of any one of these monomers and a vinyl monomer such as acrylonitrile or methyl methacrylate and/or a conjugated diene monomer such as 1,3-butadiene, isoprene, 1,3-pentadiene or 1,3-hexadiene. A graft polymer obtained by graft polymerizing styrene and/or a styrene derivative with a diene-based rubber such as polybutadiene, ethylene •propylene-based rubber or acrylic rubber, or styrene and/or a styrene derivative with another vinyl monomer may also be used.

Examples of the styrene-based resin include polystyrene, high-impact polystyrene (HIPS resin), acrylonitrile styrene copolymer (AS resin), acrylonitrile•butadiene•styrene copolymer (ABS resin), methyl methacrylate•butadiene•styrene copolymer (MBS resin), methyl methacrylate•acrylonitrile•butadiene•styrene copolymer (MABS resin), acrylonitrile•acrylic rubber•styrene copolymer (AAS resin), acrylonitrile•ethylene propylene-based rubber•styrene copolymer (AES resin) and mixtures thereof.

A hydrogenated styrene-based terpolymer obtained by hydrogenating a copolymer of the above aromatic vinyl monomer and conjugated diene comonomer may also be used. The hydrogenated styrene-based terpolymer is obtained by hydrogenating a polymer containing a conjugated diene in the recurring unit. Examples of the polymer containing a conjugated diene in the recurring unit which is preferably used in the present invention include a styrene-butadiene copolymer, styrene-isoprene copolymer and styrene-isopentadiene copolymer. The hydrogenation method is not particularly limited and can be carried out based on the prior art disclosed, for example, by JP-A 2007-301449. Examples of the hydrogenated styrene-based terpolymer include a styrene-ethylene-butylene-styrene terpolymer (SEBS) obtained by hydrogenating a styrene-butadiene copolymer, styrene-ethylene-propylene-styrene terpolymer (SEPS) obtained by hydrogenating a styrene-isoprene copolymer, and styrene-ethylene-propylene-styrene terpolymer (SEEPS) obtained by hydrogenating a styrene-isopentadiene copolymer.

The method of polymerizing the styrene-based resin is not particularly limited, and a styrene-based resin produced by the prior art such as anion polymerization, cation polymerization, free group polymerization, ligand polymerization, solution polymerization, emulsion polymerization, bulk polymerization or suspension polymerization may be used.

A rubber modified styrene-based resin (high-impact polystyrene) prepared by graft polymerizing a polymer of an aromatic vinyl monomer or a copolymer of an aromatic vinyl monomer and a vinyl monomer with a rubber-like polymer refers to a polymer which contains the particulate rubber-like polymer dispersed in a matrix and is obtained by adding the aromatic vinyl monomer and optionally the vinyl monomer in the presence of the rubber-like polymer to carry out the known bulk polymerization, bulk suspension polymerization, solution polymerization or emulsion polymerization of the obtained monomer mixture.

Examples of the above rubber-like polymer include diene-based rubbers such as polybutadiene, poly (styrene-butadiene) and poly(acrylonitrile-butadiene), saturated rubbers obtained by hydrogenating the above diene-based rubbers, isoprene rubber, chloroprene rubber, acrylic rubbers such as butyl polyacrylate, and ethylene-propylene-diene monomer terpolymer (EPDM), out of which diene-based rubbers are particularly preferred.

Examples of the aromatic vinyl monomer which is an essential ingredient of the graft copolymerizable monomer mixture to be polymerized in the presence of the above rubber-like polymer include styrene, α-methylstyrene and paramethyl styrene, out of which styrene is most preferred.

Examples of the vinyl monomer which can be optionally added include acrylonitrile and methyl methacrylate.

The content of the rubber-like polymer in the rubber modified styrene resin is 1 to 80 wt %, preferably 2 to 70 wt %. The content of the graft polymerizable monomer mixture is 99 to 20 wt %, preferably 98 to 30 wt %.

The styrene-based resin, especially high-impact polystyrene used as the component B in the present invention has an MVR value measured at 200° C. under a load of 5 kg in accordance with JIS-K-7210-1999 of preferably 1 to 100 $cm^3/10$ min, more preferably 2 to 80 $cm^3/10$ min, much more preferably 3 to 60 $cm^3/10$ min, particularly preferably 5 to 50 $cm^3/10$ min.

The styrene-based resin (component B), especially AS resin and ABS resin have an MVR value measured at 220° C. under a load of 10 kg in accordance with JIS-K-7210-1999 of preferably 1 to 100 $cm^3/10$ min, more preferably 2 to 80 $cm^3/10$ min, much more preferably 3 to 60 $cm^3/10$ min, particularly preferably 5 to 50 $cm^3/10$ min.

When the MVR value of the styrene-based resin (component B) is smaller than 1 $cm^3/10$ min, the processability at the time of extrusion or molding of the resin composition degrades and when the MVR value is larger than 100 $cm^3/10$ min, the heat resistance and mechanical properties of the resin composition deteriorate.

The styrene-based resin (component B) has a reduced viscosity $\eta_{sp}/C$ as a measure of its molecular weight of preferably 0.2 to 1.5 dl/g, more preferably 0.3 to 1.4 dl/g, The reduced viscosity $\eta_{sp}/C$ is a value obtained by measuring a toluene solution of the styrene-based resin having a concentration of 0.5 g/100 ml at 30° C.

When the reduced viscosity $\eta_{sp}/C$ of the styrene-based resin is lower than 0.2 dl/g, the heat resistance and mechanical properties of the obtained resin composition deteriorate. When the reduced viscosity is higher than 1.5 dl/g, the processability at the time of extrusion or molding of the resin composition degrades.

Means of satisfying the above requirements for the MVR value and reduced viscosity $\eta_{sp}/C$ of the styrene-based resin is to control the amount of a polymerization initiator, the polymerization temperature and the amount of a chain transfer agent.

The content of the styrene-based resin (component B) is 1 to 100 parts by weight, preferably 5 to 90 parts by weight, more preferably 8 to 70 parts by weight, much more preferably 10 to 50 parts by weight, particularly preferably 15 to 30 parts by weight based on 100 parts by weight of the component A.

(Polycarbonate Resin: Component B)

The polycarbonate resin (component B) is obtained from an interfacial polymerization reaction between a dihydroxyaryl compound and phosgene in the presence of a solvent such as methylene chloride or from a transesterification reaction between a dihydroxyaryl compound and diphenyl carbonate. A typical example of the polycarbonate resin is a polycarbonate resin obtained from a reaction between 2,2'-bis(4-hydroxyphenyl)propane and phosgene.

Examples of the dihydroxyaryl compound as a raw material of the polycarbonate resin (component B) include bis(4-hydroxyphenyl)methane, 1,1'-bis(4-hydroxyphenyl)ethane, 2,2'-bis(4-hydroxyphenyl)propane, 2,2'-bis(4-hydroxyphenyl)butane, 2,2'-bis(4-hydroxyphenyl)octane, 2,2'-bis(4-hydroxy-3-methylphenyl)propane, 2,2'-bis(4-hydroxy-3-tert-butylphenyl)propane, 2,2'-bis(3,5-dimethyl-4-hydroxyphenyl)propane, 2,2'-bis(4-hydroxy-3-cyclohexylphenyl)propane, 2,2'-bis(4-hydroxy-3-methoxyphenyl)propane, 1,1'-bis(4-hydroxyphenyl)cyclopentane, 1,1'-bis(4-hydroxyphenyl)cyclohexane, 1,1'-bis(4-hydroxyphenyl)cyclododecane, 4,4'-dihydroxyphenyl ether, 4,4'-dihydroxy-3,3'-dimethylphenyl ether, 4,4'-dihydroxydiphenyl sulfide, 4,4'-dihydroxy-3,3'-dimethyldiphenyl sulfide, 4,4'-dihydroxydiphenyl sulfoxide, 4,4'-dihydroxydiphenyl sulfone and bis(4-hydroxyphenyl)ketone. These dihydroxyaryl compounds may be used alone or in combination of two or more.

Bisphenols which form an aromatic polycarbonate resin having high heat resistance, bis(hydroxyphenyl) alkanes such as 2,2'-bis(4-hydroxyphenyl)propane, bis(hydroxyphenyl) cycloalkanes such as bis(4-hydroxyphenyl)cyclohexane, dihydroxydiphenyl sulfide, dihydroxydiphenyl sulfone and dihydroxydiphenyl ketone are preferred dihydroxyaryl compounds. 2,2'-bis(4-hydroxyphenyl)propane which forms a bisphenol A type aromatic polycarbonate is a particularly preferred dihydroxyaryl compound.

As long as heat resistance and mechanical strength are not impaired, when a bisphenol A type aromatic polycarbonate is to be produced, part of bisphenol A may be substituted by another dihydroxyaryl compound.

The polycarbonate resin may be produced by copolymerizing an aliphatic diol compound as a comonomer. Specific examples of the aliphatic diol compound include 1,2-propanediol, 1,3-butanediol, 1,4-butanediol, 1,5-pentanediol, 1,5-hexanediol, 1,6-hexanediol, 2,2-dimethylpropane-1,3-diol, ethylene glycol, diethylene glycol, triethylene glycol, tetraethylene glycol, octaethylene glycol, dipropylene glycol, cyclobutanediol, cyclopentanediol, cyclohexanediol, cyclohexanedimethanol, 2,2-bis(4-hydroxycyclohexyl)propane, bicyclohexyl-4,4-diol, tricyclo[5.2.1.0$^{2.6}$]decane dimethanol, 3,9-bis(2-hydroxy-1,1-dimethylethyl)-2,4,8,10-tetraoxaspiro(5.5)undecane, decaline dimethanol, norbornane dimethanol and pentacyclopentadecane dimethanol.

A brief description is given of basic means for producing the polycarbonate resin (component B). In the interfacial polymerization process (solution polymerization process) in which phosgene is used as a carbonate precursor, a reaction is generally carried out in the presence of an acid binder and an organic solvent. Examples of the acid binder include alkali metal hydroxides such as sodium hydroxide and potassium hydroxide, and amine compounds such as pyridine. Examples of the organic solvent include halogenated hydrocarbons such as methylene chloride and chlorobenzene. A catalyst such as tertiary amine or quaternary amine may be used to promote the reaction. A terminal capping agent such as phenol or alkyl-substituted phenol exemplified by p-tert-butylphenol is desirably used as a molecular weight control agent. The reaction temperature is generally 0 to 40° C., the reaction time is several minutes to 5 hours, and pH during the reaction is preferably kept at 10 or more. All the terminals of the obtained molecular chain do not need to have a structure derived from the terminal capping agent.

In the transesterification reaction (melt polymerization process) in which a diester carbonate is used as a carbonate precursor, a dihydric phenol is stirred together with the diester carbonate in a predetermined ratio in the presence of an inert gas under heating, and the formed alcohol or phenol is distilled off. The reaction temperature which differs according to the boiling point of the formed alcohol or phenol is generally 120 to 350° C. The reaction is completed while the formed alcohol or phenol is distilled off by reducing the pressure from the initial stage. In the initial stage of the reaction, a terminal capping agent is added together with the dihydric phenol or in the middle of the reaction. A currently known catalyst which is used for a transesterification reaction may be used to promote the reaction. Examples of the diester carbonate used in this transesterification reaction include diphenyl carbonate, dinaphthyl carbonate, dimethyl carbonate, diethyl carbonate and dibutyl carbonate. Out of these, diphenyl carbonate is particularly preferred.

The content of the OH group existent at the terminal of the polycarbonate resin (component B) is preferably not more than 100 eq/ton, more preferably 0.5 to 70 eq/ton, much more preferably 1 to 50 eq/ton, particularly preferably 1 to 30 eq/ton, most preferably 1 to 20 eq/ton. When the content of the OH group falls within the above range, heat stability becomes excellent.

The polycarbonate resin (component B) has an MVR value measured at 300° C. under a load of 1.2 kg in accordance with JIS-K-7210-1999 of preferably 0.1 to 80 cm$^3$/10 min, more preferably 0.5 to 70 cm$^3$/10 min, much more preferably 1 to 60 cm$^3$/10 min, particularly preferably 3 to 40 cm$^3$/10 min, most preferably 5 to 20 cm$^3$/10 min. When the MVR value of the polycarbonate resin is smaller than 0.1 cm$^3$/10 min, the moldability of the resin composition greatly degrades and when the MVR value is larger than 80 cm$^3$/10 min, the mechanical properties of the resin composition deteriorate.

Means of satisfying the above requirements for the MVR value and the content of the terminal OH group of the polycarbonate resin is to control the polymerization temperature, the polymerization time and the amount of the terminal capping gent.

The content of the polycarbonate resin (component B) is 1 to 100 parts by weight, preferably 5 to 90 parts by weight, more preferably 8 to 70 parts by weight, much more preferably 10 to 50 parts by weight, particularly preferably 15 to 30 parts by weight based on 100 parts by weight of the component A.

(Organic Phosphorus Compound: Component C)

In the present invention, the organic phosphorus compound which is used as the component C is represented by the following formula (1).

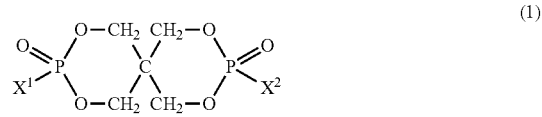
(1)

(wherein $X^1$ and $X^2$ are the same or different and each an aromatic substituted alkyl group represented by the following formula (2).)

(2)

In the above formula (2), AL is a branched or linear aliphatic hydrocarbon group having 1 to 5 carbon atoms. AL is selected from alkanediyl group having 1 to 5 carbon atoms, alkanetriyl group having 1 to 5 carbon atoms, and alkanetetrayl group having 1 to 5 carbon atoms. Specific examples thereof include methylene group, ethylene group, propylene group, butylene group, pentylene group, methanetriyl group, ethanetriyl group, propanetriyl group, butanetriyl group, pentanetriyl group, methanetetrayl group, ethanetetrayl group, propanetetrayl group, butanetetrayl group and pentanetetrayl group.

Ar is a phenyl group, naphthyl group or anthryl group all of which may have a substituent. Examples of the substituent include alkyl groups having 1 to 5 carbon atoms such as methyl group, ethyl group, propyl group and butyl group, and halogen atoms such as fluorine atom, chlorine atom and bromine atom.

"n" is an integer of 1 to 3, and Ar can be bonded to any carbon atom contained in AL.

The organic phosphorus compound is preferably at least one compound selected from the group consisting of organic phosphorus compounds represented by the following formulas (3) and (4).

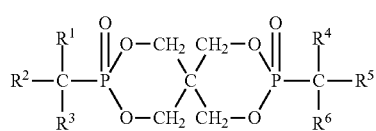

(3)

In the above formula (3), $R^2$ and $R^5$ may be the same or different and each a phenyl group, naphthyl group or anthryl group all of which may have a substituent. Examples of the substituent include alkyl groups having 1 to 5 carbon atoms such as methyl group, ethyl group, propyl group and butyl group, and halogen atoms such as fluorine atom, chlorine atom and bromine atom.

$R^1$, $R^3$, $R^4$ and $R^6$ may be the same or different and each a substituent selected from hydrogen atom, branched or linear alkyl group having 1 to 4 carbon atoms, and phenyl group, naphthyl group or anthryl group all of which may have a substituent. Examples of the branched or linear alkyl group having 1 to 4 carbon atoms include methyl group, ethyl group, propyl group and butyl group. Examples of the substituent for the phenyl group, naphthyl group or anthryl group include alkyl groups having 1 to 5 carbon atoms such as methyl group, ethyl group, propyl group and butyl group, and halogen atoms such as fluorine atom, chlorine atom and bromine atom.

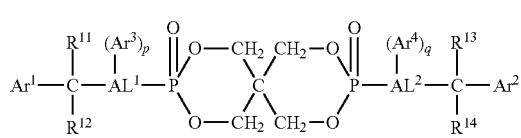

(4)

In the above formula (4), $Ar^1$ and $Ar^2$ may be the same or different and each a phenyl group, naphthyl group or anthryl group and may have a substituent in the aromatic ring.

Examples of the substituent include alkyl groups having 1 to 5 carbon atoms such as methyl group, ethyl group, propyl group and butyl group, and halogen atoms such as fluorine atom, chlorine atom and bromine atom.

$R^{11}$, $R^{12}$, $R^{13}$ and $R^{14}$ may be the same or different and each a hydrogen atom, aliphatic hydrocarbon group having 1 to 3 carbon atoms, phenyl group, naphthyl group or anthryl group and may have a substituent in the aromatic ring. Examples of the aliphatic hydrocarbon group having 1 to 3 carbon atoms include alkyl groups such as methyl group, ethyl group and propyl group. Examples of the substituent in the aromatic ring include alkyl groups having 1 to 5 carbon atoms such as methyl group, ethyl group, propyl group and butyl group, and halogen atoms such as fluorine atom, chlorine atom and bromine atom.

$AL^1$ and $AL^2$ may be the same or different and each a branched or linear aliphatic hydrocarbon group having 1 to 4 carbon atoms. The aliphatic hydrocarbon group is selected from alkanediyl group having 1 to 4 carbon atoms, alkanetriyl group having 1 to 4 carbon atoms, and alkanetetrayl group having 1 to 4 carbon atoms. Specific examples thereof include methylene group, ethylene group, propylene group, butylene group, methanetriyl group, ethanetriyl group, propanetriyl group, butanetriyl group, methanetetrayl group, ethanetetrayl group, propanetetrayl group and butanetetrayl group.

$Ar^3$ and $Ar^4$ may be the same or different and each a phenyl group, naphthyl group or anthryl group and may have a substituent in the aromatic ring. Examples of the substituent in the aromatic ring include alkyl groups having 1 to 5 carbon atoms such as methyl group, ethyl group, propyl group and butyl group, and halogen atoms such as fluorine atom, chlorine atom and bromine atom.

"p" and "q" are each an integer of 0 to 3, and $Ar^3$ and $Ar^4$ can be bonded to any carbon atom in $AL^1$ and $AL^2$, respectively.

Further, the organic phosphorus compound is more preferably any one of organic phosphorus compounds represented by the following formulas (5), (6), (7) and (8).

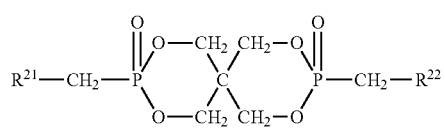

(5)

In the above formula (5), $R^{21}$ and $R^{22}$ are the same or different and each a phenyl group, naphthyl group or anthryl group and may have a substituent in the aromatic ring. Out of these, they are preferably phenyl groups. The hydrogen atom of the aromatic ring of the phenyl group represented by $R^{21}$ and $R^{22}$ may be substituted, and the substituent is a methyl group, ethyl group, propyl group, butyl group or aryl group having 6 to 14 carbon atoms and a bond to the aromatic ring through an oxygen atom, sulfur atom or aliphatic hydrocarbon group having 1 to 4 carbon atoms.

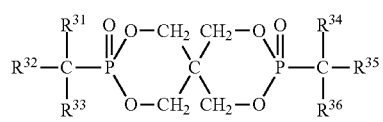

(6)

In the above formula (6), $R^{31}$ and $R^{34}$ may be the same or different and each a hydrogen atom or aliphatic hydrocarbon group having 1 to 4 carbon atoms. $R^{31}$ and $R^{34}$ are each preferably a hydrogen atom, methyl group or ethyl group, particularly preferably a hydrogen atom. $R^{33}$ and $R^{36}$ may be the same or different and each an aliphatic hydrocarbon group having 1 to 4 carbon atoms, preferably methyl group or ethyl group. $R^{32}$ and $R^{35}$ may be the same or different and each a phenyl group, naphthyl group or anthryl group and may have a substituent in the aromatic ring. They are preferably phenyl groups and may have a substituent in any part except for the part bonded to phosphorus through a carbon atom on the aromatic ring. Examples of the substituent include methyl group, ethyl group, propyl group (including an isomer thereof), butyl group (including an isomer thereof) and aryl group having 6 to 14 carbon atoms and a bond to the aromatic ring through oxygen, sulfur or aliphatic hydrocarbon group having 1 to 4 carbon atoms.

Preferred examples of $R^{32}$ and $R^{35}$ in the above formula (6) include phenyl group, cresyl group, xylyl group, trimethylphenyl group, 4-phenoxyphenyl group, cumyl group, naphthyl group and 4-benzylphenyl group. They are particularly preferably phenyl groups.

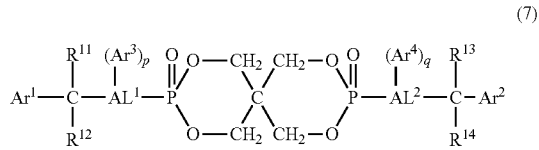
(7)

In the above formula (7), $Ar^1$ and $Ar^2$ may be the same or different and each a phenyl group, naphthyl group or anthryl group and may have a substituent in the aromatic ring. Preferred examples of $Ar^1$ and $Ar^2$ include phenyl group, cresyl group, xylyl group, trimethylphenyl group, 4-phenoxyphenyl group, cumyl group, naphthyl group and 4-benzylphenyl group. They are particularly preferably phenyl groups.

$R^{11}$, $R^{12}$, $R^{13}$ and $R^{14}$ may be the same or different and each a hydrogen atom, aliphatic hydrocarbon group having 1 to 3 carbon atoms, phenyl group, naphthyl group or anthryl group and may have a substituent in the aromatic ring. Examples of the aliphatic hydrocarbon group having 1 to 3 carbon atoms include alkyl groups having 1 to 3 carbon atoms such as methyl group, ethyl group and propyl group. $R^{11}$, $R^{12}$, $R^{13}$ and $R^{14}$ are each preferably a phenyl group having 6 to 14 carbon atoms. The phenyl group may have a substituent in any part except for the part bonded to phosphorus through a carbon atom on the aromatic ring. Examples of the substituent include methyl group, ethyl group, propyl group (including an isomer thereof), butyl group (including an isomer thereof) and aryl group having 6 to 14 carbon atoms and a bond to the aromatic ring through oxygen, sulfur or aliphatic hydrocarbon group having 1 to 4 carbon atoms.

In the above formula (7), $AL^1$ and $AL^2$ may be the same or different and each a branched or linear aliphatic hydrocarbon group having 1 to 4 carbon atoms. They are each preferably a branched or linear aliphatic hydrocarbon group having 1 to 3 carbon atoms, particularly preferably a branched or linear aliphatic hydrocarbon group having 1 to 2 carbon atoms. The aliphatic hydrocarbon group is selected from alkanediyl group having 1 to 4 carbon atoms, alkanetriyl group having 1 to 4 carbon atoms, and alkanetetrayl group having 1 to 4 carbon atoms. Specific examples thereof include methylene group, ethylene group, propylene group, butylene group, methanetriyl group, ethanetriyl group, propanetriyl group, butanetriyl group, methanetetrayl group, ethanetetrayl group, propanetetrayl group and butanetetrayl group.

In the above formula (7), preferred examples of $AL^1$ and $AL^2$ include methylene group, ethylene group, ethylidene group, trimethylene group, propylidene group and isopropylidene group, out of which methylene group, ethylene group and ethylidene group are particularly preferred.

In the formula (7), $Ar^3$ and $Ar^4$ may be the same or different and each a phenyl group, naphthyl group or anthryl group and may have a substituent in the aromatic ring. $Ar^3$ and $Ar^4$ are each preferably a phenyl group. The phenyl group may have a substituent in any part except for the part bonded to phosphorus through a carbon atom on the aromatic ring. Examples of the substituent include methyl group, ethyl group, propyl group (including an isomer thereof), butyl group (including an isomer thereof) and aryl group having 6 to 14 carbon atoms and a bond to the aromatic ring through oxygen, sulfur or aliphatic hydrocarbon group having 1 to 4 carbon atoms.

In the formula (7), "p" and "q" are each an integer of 0 to 3, and $Ar^3$ and $Ar^4$ can be bonded to any carbon atom in $AL^1$ and $AL^2$, respectively. "p" and "q" are preferably 0 or 1, particularly preferably 0.

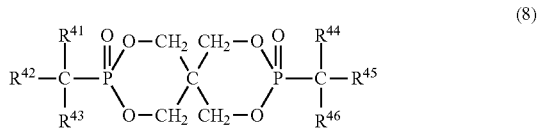
(8)

In the above formula (8), $R^{41}$ and $R^{44}$ may be the same or different and each a hydrogen atom, aliphatic hydrocarbon group having 1 to 4 carbon atoms, phenyl group, naphthyl group or anthryl group and may have a substituent in the aromatic ring. $R^{41}$ and $R^{44}$ are each preferably a hydrogen atom, aliphatic hydrocarbon group having 1 to 3 carbon atoms, or phenyl group which may have a substituent. When $R^{41}$ and $R^{44}$ are phenyl groups, they may have a substituent in any part except for the part bonded to phosphorus through a carbon atom on the aromatic ring. Examples of the substituent include methyl group, ethyl group, propyl group (including an isomer thereof), butyl group (including an isomer thereof) and aryl group having 6 to 14 carbon atoms and a bond to the aromatic ring through oxygen, sulfur or aliphatic hydrocarbon group having 1 to 4 carbon atoms.

In the formula (8), preferred examples of $R^{41}$ and $R^{44}$ include hydrogen atom, methyl group, ethyl group, propyl group (including an isomer thereof), phenyl group, cresyl group, xylyl group, trimethylphenyl group, 4-phenoxyphenyl group, cumyl group, naphthyl group and 4-benzylphenyl group, out of which hydrogen atom, methyl group and phenyl group are particularly preferred.

$R^{42}$, $R^{43}$, $R^{45}$ and $R^{46}$ may be the same or different and each a phenyl group, naphthyl group or anthryl group and may have a substituent in the aromatic ring. They are preferably phenyl groups and may have a substituent in any part except for the part bonded to phosphorus through a carbon atom on the aromatic ring. Examples of the substituent include methyl group, ethyl group, propyl group (including an isomer thereof), butyl group (including an isomer thereof) and aryl group having 6 to 14 carbon atoms and a bond to the aromatic ring through oxygen, sulfur or aliphatic hydrocarbon group having 1 to 4 carbon atoms.

In the formula (8), preferred examples of $R^{42}$, $R^{43}$, $R^{45}$ and $R^{46}$ include phenyl group, cresyl group, xylyl group, trimethylphenyl group, 4-phenoxyphenyl group, cumyl group, naphthyl group and 4-benzylphenyl group. They are particularly preferably phenyl groups.

The organic phosphorus compound (component C) represented by the formula (1) has an extremely excellent flame retarding effect for the above resin. As far as the inventors of the present invention know, the halogen-free flame retardation of the resin has been difficult with a small amount of a flame retardant and has had a large number of problems to be solved for practical use.

However, according to the present invention, surprisingly, the flame retardation of the resin is easily attained by using only the above organic phosphorus compound (component C)

in a small amount without impairing the characteristic properties, especially heat resistance of the resin.

In the present invention, in addition to the component C, a phosphorus compound except for the component C, a fluorine-containing resin or another additive may be used naturally in order to reduce the amount of the component C and improve the flame retardancy, physical properties and chemical properties of a molded article and for other purposes.

Although the organic phosphorus compound (component C) as a flame retardant in the flame retardant resin composition of the present invention is represented by the above formula (1), the most preferred typical organic phosphorus compound is an organic phosphorus compound represented by the following formula (1-a), (1-b), (1-c) or (1-d).

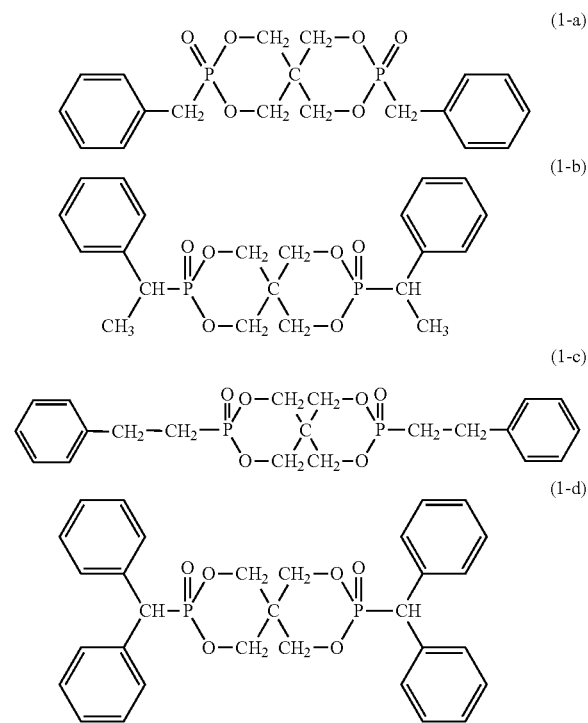

A description is subsequently given of the method of synthesizing the organic phosphorus compound (component C) in the present invention. The component C may be produced by a method other than the methods described below.

The component C is obtained, for example, by reacting phosphorus trichloride with pentaerythritol, treating the oxidized reaction product with an alkali metal compound such as sodium methoxide, and reacting the treated product with an aralkyl halide.

The component C may also be obtained by a method in which pentaerythritol is reacted with aralkyl phosphonic acid dichloride, or a method in which pentaerythritol is reacted with phosphorus trichloride and then the obtained compound is reacted with an aralkyl alcohol to carry out an Arbuzov reaction at a high temperature. The latter reaction is disclosed by U.S. Pat. No. 3,141,032, JP-A 54-157156 and JP-A 53-39698.

A specific method of synthesizing the component C will be described hereinbelow, and this method is just given for explanation. The component C used in the present invention may be synthesized not only by this method but also by its modified method or another method. More specific synthesizing methods will be described in Preparation Examples which are given hereinafter.

(I) Organic Phosphorus Compound (1-a) Out of Components C:

This compound can be obtained by reacting pentaerythritol with phosphorus trichloride, treating the reaction product oxidized by tertiary butanol with sodium methoxide, and reacting the treated product with benzyl bromide.

(II) Organic Phosphorus Compound (1-b) Out of Components C:

This compound can be obtained by reacting pentaerythritol with phosphorus trichloride, treating the reaction product oxidized by tertiary butanol with sodium methoxide, and reacting the treated product with 1-phenylethyl bromide.

(III) Organic Phosphorus Compound (1-c) Out of Components C:

This compound can be obtained by reacting pentaerythritol with phosphorus trichloride, treating the reaction product oxidized by tertiary butanol with sodium methoxide, and reacting the treated product with 2-phenylethyl bromide.

(IV) Organic Phosphorus Compound (1-d) Out of Components C:

This compound can be obtained by reacting pentaerythritol with diphenylmethyl phosphonic acid dichloride.

As an alternative method, the organic phosphorus compound is obtained by reacting pentaerythritol with phosphorus trichloride and heating a reaction product of the obtained product and diphenyl methyl alcohol in the presence of a catalyst.

The acid value of the above-described component C is not more than 0.7 mgKOH/g, preferably not more than 0.5 mgKOH/g. By using the component C having an acid value within this range, a molded article which is excellent in flame retardancy and color and has high heat stability is obtained. The acid value of the component B is most preferably not more than 0.4 mgKOH/g. The term "acid value" means the amount of KOH required for neutralizing the acid component contained in 1 g of a sample (component C).

Further, the component C having an HPLC purity of preferably at least 90%, more preferably at least 95% is used. The component C having such high purity is excellent in the flame retardancy, color and heat stability of a molded article obtained therefrom. The HPLC purity of the component B can be effectively measured by the following method.

The Develosil ODS-7 having a length of 300 mm and a diameter of 4 mm of Nomura Chemical Co., Ltd. was used as a column, and the column temperature was set to 40° C. A mixed solution of acetonitrile and water in a volume ratio of 6:4 was used as a solvent, and 5 µl of the solution was injected. UN-260 nm was used as a detector.

Although the method of removing impurities contained in the component B is not particularly limited, a method in which repulp cleaning (cleaning with a solvent and filtration are repeated several times) is carried out with a solvent such as water or methanol is the most effective and economically advantageous.

The content of the above component C is 1 to 100 parts by weight, preferably 5 to 90 parts by weight, more preferably 10 to 70 parts by weight, particularly preferably 15 to 50 parts by weight based on 100 parts by weight of the polylactic acid and/or lactic acid copolymer component (component A). The preferred range of the content of the component C is determined according to a desired level of flame retardancy and the types of the resin components (components A and B). Components other than the components A, B and C constituting the composition may be optionally used as long as the object of the present invention is not impaired, and the content of the component C can be changed by using another flame retardant, a retarding aid or a fluorine-containing resin. In most cases, the content of the component C can be reduced by using these substances.

For the preparation of the flame retardant resin composition of the present invention, a method in which the resin components (components A and B) and the organic phosphorus compound (component C) and optionally other components are premixed together by means of a mixer such as twin-cylinder mixer, super mixer, super floater or Henschel mixer, and the premixture is supplied into a kneading machine to be molten and mixed is preferably employed. A melt mixer such as a kneader, or a single-screw or double-screw extruder may be used as the kneading machine. A method in which a double-screw extruder is used to melt the resin composition at 150 to 300° C., preferably 170 to 280° C., a liquid component is injected by a side feeder, and the resulting mixture is extruded and pelletized with a pelletizer is particularly preferably employed.

The flame retardant resin composition of the present invention contains substantially no halogen, has extremely high flame retardancy and is useful as a material for molding various molded articles such as home electric appliance parts, electric and electronic parts, auto parts, mechanical and electromechanical parts, and cosmetic containers. More specifically, it can be advantageously used for breaker parts, switch parts, motor parts, ignition coil cases, power plugs, power receptacles, coil bobbins, connectors, relay cases, fuse cases, flyback transformer parts, focus block parts, distributor caps and harness connectors. Further, it is useful as a material for molding housings, casings and chassis which are becoming thinner, for example, for electric and electronic products (for example, home electric appliances and OA equipment, such as telephones, personal computers, printers, facsimiles, copiers, TV sets, video decks and audio equipment, and parts thereof). It is particularly useful as a material for molding mechanical and electromechanical parts for home electric appliances and OA equipment, such as printer housings, fixing unit parts and facsimiles which require excellent heat resistance and flame retardancy.

The molding technique is not particularly limited and may be injection molding, blow molding or press molding. However, preferably, a pellet resin composition is injection molded by using an injection molding machine.

EXAMPLES

The following examples are provided for the purpose of further illustrating the present invention but are in no way to be taken as limiting. Evaluations were made by the following methods.
(1) Flame Retardancy (UL-94 Rating)
A test piece having a thickness of 1/16 inch (1.6 mm) was used to evaluate its flame retardancy in accordance with a vertical burn test specified in US UL-94 standards as a measure of evaluating flame retardancy.

The UL-94 vertical burn test is made on a set of five test pieces, and a flame is applied to each of the specimens for 10 seconds two times. This is not applied to a test piece which is burnt down with the first flame application. After a first time of flaming combustion, the combustion time after the flame is removed is measured, and a second flame is applied after extinction. After the second flame application, the combustion time after the flame is removed is measured. A total of 10 combustion times can be measured by tests on a set of five specimens. When each burning stops within 10 seconds, the total of 10 combustion times is 50 seconds or less, and cotton is not ignited by flaming drips from any specimen, the specimen is rated V-0. When each burning stops within 30 seconds, the total of 10 combustion times is 250 seconds or less, and cotton is not ignited by flaming drips from any specimen, the specimen is rated V-1. When each burning stops within 30 seconds, the total of 10 combustion times is 250 seconds or less, and cotton is ignited by flaming drips from any specimen, the specimen is rated V-2. A specimen rated below this is designated as "not V".

As for V-2, the extinction time of flaming drips formed by first flame application was measured and evaluated based on the following criteria.
◯: extinction time of flaming drips is less than 30 seconds
X: extinction time of flaming drips is 30 seconds or longer
(2) Heat Resistance (Deflection Temperature Under Load; HDT)
A test piece having a thickness of 6.35 mm (¼ inch) was used to measure its deflection temperature under a load of 0.45 MPa in accordance with the method specified in ISO5-2. The retention (M) of the deflection temperature under load was calculated from the formula $M=(y/x)\times 100(\%)$ by measuring the deflection temperature under load ($x(°C.)$) of a molded article of a base resin in use (a mixture of the components A and B) and the deflection temperature under load ($y(°C.)$) of a molded article of a flame retardant resin composition (a mixture of the base resin and the component C).
(3) Acid Value of Organic Phosphorus Compound
This was measured in accordance with JIS-K-3504.
(4) HPLC Purity of Organic Phosphorus Compound
A sample was dissolved in a mixed solution of acetonitrile and water in a volume ratio of 6:4, and 5 µl of the resulting solution was injected into a column. The Develosil ODS-7 having a thickness of 300 mm and a diameter of 4 mm of Nomura Chemical Co., Ltd. was used as the column, and the column temperature was set to 40° C. UV-260 nm was used as a detector.
(5) $^{31}$P-NMR Purity of Organic Phosphorus Compound
The nuclear magnetic resonance of a phosphorus atom was measured with a nuclear magnetic resonance measuring instrument (JNM-AL400 of JEOL Ltd.) (DMSO-$d_6$, 162 MHz, integrated number of times: 3,072) and the integral area ratio was taken as the $^{31}$P-NMR purity of the phosphorus compound.
(6) MVR of Styrene-Based Resin
This was measured at 200° C. under a load of 5 kg or at 220° C. under a load of 10 kg in accordance with JIS-K-7210-1999.
(7) MVR of Polycarbonate Resin
This was measured at 300° C. under a load of 1.2 kg in accordance with JIS-K-7210-1999.
(8) Amount of Terminal OH Group of Polycarbonate Resin
The amount of the terminal OH group of the polycarbonate resin was calculated from the integral value of H peaks at the aromatic ortho-position having a terminal OH group and the integral value of satellite peaks of H peaks at the aromatic ortho-position of the polycarbonate by $^1$H-NMR (JNM-AL400 of JEOL Ltd.) at 400 MHz.

Preparation Example 1

Preparation of 2,4,8,10-tetraoxa-3,9-diphosphaspiro[5.5]undecane, 3,9-dibenzyl-3,9-dioxide (FR-1)

816.9 g (6.0 moles) of pentaerythritol, 19.0 g (0.24 mole) of pyridine and 2,250.4 g (24.4 moles) of toluene were fed to a reactor equipped with a thermometer, condenser and dropping funnel and stirred. 1,651.8 g (12.0 moles) of phosphorus trichloride was added to the reactor by using the dropping funnel and then heated at 60° C. under agitation after addition. After a reaction, the reactor was cooled to room temperature, 26.50 parts of methylene chloride was added to the obtained reaction product, and 889.4 g (12.0 moles) of tertiary butanol and 150.2 g (1.77 moles) of methylene chloride were added dropwise under cooling with ice. The obtained crystal was cleaned with toluene and methylene chloride and filtered. The obtained filtrate was dried at 80° C. and $1.33 \times 10^2$ Pa for 12 hours to obtain 1,341.1 g (5.88 moles) of a white solid. It was confirmed by $^{31}$P- and $^1$H-NMR spectra that the obtained solid was 2,4,8,10-tetraoxa-3,9-diphosphaspiro[5.5]undecane, 3,9-dihydro-3,9-dioxide.

1,341.0 g (5.88 moles) of the obtained 2,4,8,10-tetraoxa-3,9-diphosphaspiro[5.5]undecane, 3,9-dihydro-3,9-dioxide and 6,534.2 g (89.39 moles) of DMF were fed to a reactor equipped with a thermometer, condenser and dropping funnel and stirred. 648.7 g (12.01 moles) of sodium methoxide was added to the reactor under cooling with ice. After 2 hours of stirring under cooling with ice, they were stirred at room temperature for 5 hours. Further, after DMF was distilled off, 2,613.7 g (35.76 moles) of DMF was added, and 2,037.79 g (11.91 moles) of benzyl bromide was added dropwise to the reaction mixture under cooling with ice. After 3 hours of stirring under cooling with ice, DMF was distilled off, 8 liters of water was added, and the precipitated solid was separated by filtration and cleaned with 2 liters of water twice. The obtained roughly purified product and 4 liters of methanol were put into a reactor equipped with a condenser and stirrer and refluxed for about 2 hours. After the reactor was cooled to room temperature, the crystal was separated by filtration and cleaned with 2 liters of methanol, and the obtained filtrate was dried at 120° C. and $1.33 \times 10^2$ Pa for 19 hours to obtain 1,863.5 g (4.56 moles) of a white flaky crystal. It was confirmed by $^{31}$P- and $^1$H-NMR spectra and elemental analysis that the obtained crystal was 2,4,8,10-tetraoxa-3,9-diphosphaspiro[5.5]undecane, 3,9-dibenzyl-3,9-dioxide. The yield rate was 76%, and the $^{31}$P-NMR purity was 99%. The HPLC purity measured by the method of this text was 99%. The acid value was 0.06 mgKOH/g. $^1$H-NMR (DMSO-$d_6$, 300 MHz): δ7.2-7.4 (m, 10H), 4.1-4.5 (m, 8H), 3.5 (d, 4H), $^{31}$P-NMR (DMSO-$d_6$, 120 MHz): 523.1 (S), melting point: 255-256° C., elemental analysis calculated values: C, 55.89; H, 5.43, measurement values: C, 56.24; H, 5.35

Preparation Example 2

Preparation of 2,4,8,10-tetraoxa-3,9-diphosphaspiro [5.5]undecane, 3,9-dibenzyl-3,9-dioxide (FR-2)

22.55 g (0.055 mole) of 3,9-dibenzyloxy-2,4,8,10-tetraoxa-3,9-diphosphaspiro [5.5]undecane, 19.01 g (0.11 mole) of benzyl bromide and 33.54 g (0.32 mole) of xylene were charged into a reactor equipped with a stirrer, thermometer and condenser, and dry nitrogen was let flow into the reactor under agitation at room temperature. Then, heating was started with an oil bath, and the reaction mixture was heated at a reflux temperature (about 130° C.) under agitation for 4 hours. After heating, the reaction product was left to be cooled to room temperature, and 20 ml of xylene was added and further stirred for 30 minutes. The precipitated crystal was separated by filtration and cleaned with 20 ml of xylene twice. The obtained roughly purified product and 40 ml of methanol were put into a reactor equipped with a condenser and stirrer and refluxed for about 2 hours. After cooling to room temperature, the crystal was separated by filtration and cleaned with 20 ml of methanol, and the obtained filtrate was dried at 120° C. and $1.33 \times 10^2$ Pa for 19 hours to obtain a white flaky crystal. It was confirmed by the mass spectral analysis, $^1$H and $^{31}$P nuclear magnetic resonance spectral analysis and elemental analysis that the product was bisbenzylpentaerythritol diphosphonate. The yield was 20.60 g, the yield rate was 91 and the $^{31}$P-NMR purity was 99%. The HPLC purity measured by the method of this text was 99%. The acid value was 0.05 mgKOH/g.

$^1$H-NMR (DMSO-$d_6$, 300 MHz): δ7.2-7.4 (m, 10H), 4.1-4.5 (m, 8H), 3.5 (d, 4H), $^{31}$P-NMR (DMSO-$d_6$, 120 MHz): 823.1 (S), melting point: 257° C.

Preparation Example 3

Preparation of 2,4,8,10-tetraoxa-3,9-diphosphaspiro [5.5]undecane, 3,9-diα-methylbenzyl-3,9-dioxide (FR-3)

816.9 g (6.0 moles) of pentaerythritol, 19.0 g (0.24 mole) of pyridine and 2,250.4 g (24.4 moles) of toluene were fed to a reactor equipped with a thermometer, condenser and dropping funnel and stirred. 1,651.8 g (12.0 moles) of phosphorus trichloride was added to the reactor by using the dropping funnel and then heated at 60° C. under agitation after addition. After a reaction, the reactor was cooled to room temperature, 5,180.7 g (61.0 moles) of methylene chloride was added to the obtained reaction product, and 889.4 g (12.0 moles) of tertiary butanol and 150.2 g (1.77 moles) of methylene chloride were added dropwise under cooling with ice. The obtained crystal was cleaned with toluene and methylene chloride and filtered. The obtained filtrate was dried at 80° C. and $1.33 \times 10^2$ Pa for 12 hours to obtain 1,341.1 g (5.88 moles) of a white solid. It was confirmed by $^{31}$P and $^1$HNMR spectra that the obtained solid was 2,4,8,10-tetraoxa-3,9-diphosphaspiro[5.5]undecane, 3,9-dihydro-3,9-dioxide.

1,341.0 g (5.88 moles) of the obtained 2,4,8,10-tetraoxa-3,9-diphosphaspiro[5.5]undecane 3,9-dihydro-3,9-dioxide and 6,534.2 g (89.39 moles) of DMF were fed to a reactor equipped with a thermometer, condenser and dropping funnel and stirred. 648.7 g (12.01 moles) of sodium methoxide was added to the reactor under cooling with ice. After 2 hours of stirring under cooling with ice, they were stirred at room temperature for 5 hours. Further, after DMF was distilled off, 2,613.7 g (35.76 moles) of DMF was added, and 2,204.06 g (11.91 moles) of 1-phenylethyl bromide was added dropwise to the reaction mixture under cooling with ice. After 3 hours of stirring under cooling with ice, DMF was distilled off, 8 liters of water was added, and the precipitated solid was separated by filtration and cleaned with 2 liters of water twice. The obtained roughly purified product and 4 liters of methanol were put into a reactor equipped with a condenser and stirrer and refluxed for about 2 hours. After the reactor was cooled to room temperature, the crystal was separated by filtration and cleaned with 2 liters of methanol, and the obtained filtrate was dried at 120° C. and $1.33 \times 10^2$ Pa for 19 hours to obtain 1,845.9 g (4.23 moles) of a white flaky crystal. It was confirmed by $^{31}$P-NMR and $^1$H-NMR spectra and elemental analysis that the obtained solid was 2,4,8,10-tetraoxa-3,9-diphosphaspiro[5.5]undecane, 3,9-diα-methylbenzyl-3,9-dioxide. The $^{31}$P-NMR purity was 99%. The HPLC purity measured by the method of this text was 99%. The acid value was 0.03 mgKOH/g.

$^1$H-NMR (CDCl$_3$, 300 MHz): δ7.2-7.4 (m, 10H), 4.0-4.2 (m, 4H), 3.4-3.8 (m, 4H), 3.3 (qd, 4H), 1.6 (ddd, 6H), $^{31}$P-NMR (CDCl$_3$, 120 MHz): 628.7 (S), melting point: 190-210°

C., elemental analysis calculated values: C, 57.80; H, 6.01, measurement values: C, 57.83; H, 5.96

Preparation Example 4

Preparation of 2,4,8,10-tetraoxa-3,9-diphosphaspiro [5.5]undecane, 3,9-di(2-phenylethyl)-3,9-dioxide (FR-4)

816.9 g (6.0 moles) of pentaerythritol, 19.0 g (0.24 mole) of pyridine and 2,250.4 g (24.4 moles) of toluene were fed to a reactor equipped with a thermometer, condenser and dropping funnel and stirred. 1,651.8 g (12.0 moles) of phosphorus trichloride was added to the reactor by using the dropping funnel and then heated at 60° C. under agitation after addition. After a reaction, the reactor was cooled to room temperature, 5,180.7 g (61.0 moles) of methylene chloride was added to the obtained reaction product, and 889.4 g (12.0 moles) of tertiary butanol and 150.2 g (1.77 moles) of methylene chloride were added dropwise under cooling with ice. The obtained crystal was cleaned with toluene and methylene chloride and filtered. The obtained filtrate was dried at 80° C. and $1.33 \times 10^2$ Pa for 12 hours to obtain 1,341.1 g (5.88 moles) of a white solid. It was confirmed by $^{31}$P and $^1$H-NMR spectra that the obtained solid was 2,4,8,10-tetraoxa-3,9-diphosphaspiro[5.5]undecane, 3,9-dihydro-3,9-dioxide.

1,341.0 g (5.88 moles) of the obtained 2,4,8,10-tetraoxa-3,9-diphosphaspiro[5.5]undecane, 3,9-dihydro-3,9-dioxide and 6,534.2 g (89.39 moles) of DMF were fed to a reactor equipped with a thermometer, condenser and dropping funnel and stirred. 648.7 g (12.01 moles) of sodium methoxide was added to the reactor under cooling with ice. After 2 hours of stirring under cooling with ice, they were stirred at room temperature for 5 hours. After DMF was distilled off, 2,613.7 g (35.76 moles) of DMF was added, and 2,183.8 g (11.8 moles) of (2-bromoethyl)benzene was added dropwise to the reaction mixture under cooling with ice. After 3 hours of stirring under cooling with ice, DMF was distilled off, 8 liters of water was added, and the precipitated solid was separated by filtration and cleaned with 2 liters of water twice. The obtained roughly purified product and 4 liters of methanol were put into a reactor equipped with a condenser and stirrer and refluxed for about 2 hours. After the reactor was cooled to room temperature, the crystal was separated by filtration and cleaned with 2 liters of methanol, and the obtained filtrate was dried at 120° C. and $1.33 \times 10^2$ Pa for 19 hours to obtain 1,924.4 g (4.41 moles) of a white powder. It was confirmed by $^{31}$P-NMR and $^1$H-NMR spectra and elemental analysis that the obtained solid was 2,4,8,10-tetraoxa-3,9-diphosphaspiro [5.5]undecane, 3,9-di(2-phenylethyl)-3,9-dioxide. The $^{31}$P-NMR purity was 99%. The HPLC purity measured by the method of this text was 99%. The acid value was 0.03 mgKOH/g.

$^1$H-NMR (CDCl$_3$, 300 MHz): δ7.1-7.4 (m, 10H), 3.85-4.65 (m, 8H), 2.90-3.05 (m, 4H), 2.1-2.3 (m, 4H), $^{31}$P-NMR (CDCl$_3$, 120 MHz): δ31.5 (S), melting point: 245-246° C., elemental analysis calculated values: C, 57.80; H, 6.01, measurement values: C, 58.00; H, 6.07

Preparation Example 5

Preparation of 2,4,8,10-tetraoxa-3,9-diphosphaspiro [5.5]undecane, 3,9-bis(diphenylmethyl)-3,9-dioxide (FR-5)

2,058.5 g (7.22 moles) of diphenylmethyl phosphonic acid dichloride, 468.3 g (3.44 moles) of pentaerythritol, 1,169.4 g (14.8 moles) of pyridine and 8,200 g of chloroform were fed to a 10-liter three-necked flask equipped with a stirrer, agitation blade, reflux condenser and thermometer, heated at 60° C. in a nitrogen gas stream and stirred for 6 hours. After the end of a reaction, chloroform was substituted by methylene chloride, and 6 liters of distilled water was added to the reaction mixture and stirred to precipitate a white powder. The white powder was separated by suction filtration, and the obtained white product was cleaned with methanol and dried at 100° C. and $1.33 \times 10^2$ Pa for 10 hours to obtain 1,156.2 g of a white solid. It was confirmed by $^{31}$P-NMR and $^1$P-NMR spectra and elemental analysis that the obtained solid was 2,4,8,10-tetraoxa-3,9-diphosphaspiro[5.5]undecane, 3,9-bis (diphenylmethyl)-3,9-dioxide. The $^{31}$P-NMR purity was 99%. The HPLC purity measured by the method of this text was 99%. The acid value was 0.3 mgKOH/g.

$^1$H-NMR (DMSO-d$_6$, 300 MHz): δ7.20-7.60 (m, 20H), 5.25 (d, 2H), 4.15-4.55 (m, 8H), $^{31}$P-NMR (DMSO-d$_6$, 120 MHz): δ20.9, melting point: 265° C., elemental analysis calculated values: C, 66.43; H, 5.39, measurement values: C, 66.14; H. 5.41

Components used in Examples and Comparative Examples are given below.
(I) Polylactic Acid Resin (Component A)
(i) Commercially available polylactic acid (4032D of Nature Works Co., Ltd.; poly-L-lactic acid resin) (to be referred to as "PLA-1" hereinafter)
(ii) Commercially available polylactic acid (LACEA H100 of Mitsui Chemical Co., Ltd.; poly-L-lactic acid resin) (to be referred to as "PLA-2" hereinafter)
(II) Styrene-Based Resin (Component B)
(i) Commercially available high-impact polystyrene (PSJ Polystyrene H9152 of PS Japan Co., Ltd.) (to be referred to as "HIPS", MVR value at 200° C. under a load of 5 kg of 5.7 cm$^3$/10 min)
(ii) Commercially available ABS resin (Suntac UT-61 of Japan A and L Co., Ltd.) (to be referred to as "ABS" hereinafter, MVR value at 220° C. under a load of 10 kg of 35 cm$^3$/10 min)
(iii) Commercially available AS resin (Litac-A BS-203 of Nippon A&L Inc.) (to be referred to as "AS" hereinafter, MVR value at 220° C. under a load of 10 kg of 18 cm$^3$/10 min)
(III) Polycarbonate Resin (Component B)
(i) commercially available polycarbonate resin (Panlite L-1225 of Teijin Chemicals Ltd.) (to be referred to as "PC-1" hereinafter, terminal OH group content of 14 eq/ton, MVR value at 300° C. under a load of 1.2 kg of 10.1 cm$^3$/10 min)
(ii) commercially available polycarbonate resin (Panlite L-1250 of Teijin Chemicals Ltd.) (to be referred to as "PC-2" hereinafter, terminal OH group content of 13 eq/ton, MVR value measured at 300° C. under a load of 1.2 kg of 7.5 cm$^3$/10 min)
(IV) Organic Phosphorus Compound (Component C)
(i) 2,4,8,10-tetraoxa-3,9-diphosphaspiro[5.5]undecane, 3,9-di benzyl-3,9-dioxide synthesized in Preparation Example 1 {organic phosphorus compound represented by the above formula (1-a) (to be referred to as "FR-1" hereinafter)}
(ii) 2,4,8,10-tetraoxa-3,9-diphosphaspiro[5.5]undecane, 3,9-di benzyl-3,9-dioxide synthesized in Preparation Example 2 {organic phosphorus compound represented by the above formula (1-a) (to be referred to as "FR-2" hereinafter)}
(iii) 2,4,8,10-tetraoxa-3,9-diphosphaspiro[5.5]undecane, 3,9-di α-methylbenzyl-3,9-dioxide synthesized in Preparation Example 3 {organic phosphorus compound represented by the above formula (1-b) (to be referred to as "FR-3" hereinafter)}

(iv) 2,4,8,10-tetraoxa-3,9-diphosphaspiro[5.5]undecane, 3,9-di (2-phenylethyl)-3,9-dioxide synthesized in Preparation Example 4 {organic phosphorus compound represented by the above formula (1-c) (to be referred to as "FR-4" hereinafter)}

(v) 2,4,8,10-tetraoxa-3,9-diphosphaspiro[5.5]undecane, 3,9-bis(diphenylmethyl)-3,9-dioxide synthesized in Preparation Example 5 {organic phosphorus compound represented by the above formula (1-d) (to be referred to as "FR-5" hereinafter)}

(V) Other Organic Phosphorus Compound (i) 1,3-phenylenebis[di(2,6-dimethylphenyl)phosphate] (PX-200 of Daihachi Chemical Industry Co., Ltd.) (to be referred to as "PX-200" hereinafter)

Examples 1 to 24 and Comparative Examples 1 to 12

The amounts (parts by weight) shown in Tables 1 to 3 of components shown in Tables 1 to 3 were mixed together by means of a tumbler, and the resulting mixtures were pelletized by means of a 15 mm$\phi$ double-screw extruder (KZW15 of Technovel Corporation). The obtained pellets were dried with a hot air drier at 80° C. for 24 hours. The dried pellets were molded by means of an injection molding machine (J75EIII of The Japan Steel Works, Ltd.). The evaluation results of the molded plates are shown in Tables 1 to 3.

TABLE 1

| | Component | Unit | Ex. 1 | Ex. 2 | Ex. 3 | Ex. 4 | Ex. 5 | Ex. 6 | Ex. 7 | Ex. 8 |
|---|---|---|---|---|---|---|---|---|---|---|
| Composition | Component A | Type | PLA-1 | PLA-1 | PLA-1 | PLA-1 | PLA-1 | PLA-1 | PLA-1 | PLA-1 |
| | | Parts by weight | 100 | 100 | 100 | 100 | 100 | 100 | 100 | 100 |
| | Component B | Type | HIPS | ABS | AS | HIPS | ABS | AS | HIPS | ABS |
| | | Parts by weight | 15 | 15 | 15 | 20 | 20 | 20 | 15 | 15 |
| | Component C | Type | FR-1 | FR-1 | FR-1 | FR-1 | FR-1 | FR-1 | FR-1 | FR-1 |
| | | Parts by weight | 20 | 20 | 20 | 20 | 20 | 20 | 30 | 30 |
| Flame retardancy | UL-94 test | Thickness of test piece | 1.6 mm | 1.6 mm | 1.6 mm | 1.6 mm | 1.6 mm | 1.6 mm | 1.6 mm | 1.6 mm |
| | | UL rating | V-2 | V-2 | V-0 | V-2 | V-2 | V-2 | V-0 | V-0 |
| | | Drips | ○ | ○ | — | ○ | ○ | ○ | — | — |
| HDT | ISO 75-2 | ° C. | 56 | 57 | 58 | 58 | 58 | 59 | 58 | 58 |
| | 0.45 MPa | Retention (%) | 100 | 100 | 102 | 104 | 102 | 102 | 104 | 102 |

| | Component | Unit | Ex. 9 | Ex. 10 | Ex. 11 | Ex. 12 | Ex. 13 | Ex. 14 | Ex. 15 |
|---|---|---|---|---|---|---|---|---|---|
| Composition | Component A | Type | PLA-1 | PLA-1 | PLA-1 | PLA-1 | PLA-1 | PLA-1 | PLA-1 |
| | | Parts by weight | 100 | 100 | 100 | 100 | 100 | 100 | 100 |
| | Component B | Type | AS | HIPS | ABS | AS | HIPS | ABS | AS |
| | | Parts by weight | 15 | 20 | 20 | 20 | 20 | 20 | 20 |
| | Component C | Type | FR-1 | FR-1 | FR-1 | FR-1 | FR-2 | FR-2 | FR-2 |
| | | Parts by weight | 30 | 30 | 30 | 30 | 30 | 30 | 30 |
| Flame retardancy | UL-94 test | Thickness of test piece | 1.6 mm | 1.6 mm | 1.6 mm | 1.6 mm | 1.6 mm | 1.6 mm | 1.6 mm |
| | | UL rating | V-0 | V-0 | V-0 | V-0 | V-0 | V-0 | V-0 |
| | | Drips | — | — | — | — | — | — | — |
| HDT | ISO 75-2 | ° C. | 58 | 57 | 57 | 59 | 57 | 57 | 58 |
| | 0.45 MPa | Retention (%) | 102 | 102 | 100 | 102 | 102 | 100 | 100 |

Ex.: Example

TABLE 2

| | Component | Unit | Ex. 16 | Ex. 17 | Ex. 18 | Ex. 19 | Ex. 20 | Ex. 21 | Ex. 22 | Ex. 23 | Ex. 24 |
|---|---|---|---|---|---|---|---|---|---|---|---|
| Composition | Component A | Type | PLA-1 | PLA-1 | PLA-1 | PLA-1 | PLA-1 | PLA-1 | PLA-1 | PLA-1 | PLA-1 |
| | | Parts by weight | 100 | 100 | 100 | 100 | 100 | 100 | 100 | 100 | 100 |
| | Component B | Type | HIPS | ABS | AS | HIPS | ABS | AS | HIPS | ABS | AS |
| | | Parts by weight | 20 | 20 | 20 | 20 | 20 | 20 | 20 | 20 | 20 |
| | Component C | Type | FR-3 | FR-3 | FR-3 | FR-4 | FR-4 | FR-4 | FR-5 | FR-5 | FR-5 |
| | | Parts by weight | 30 | 30 | 30 | 30 | 30 | 30 | 30 | 30 | 30 |
| Flame retardancy | UL-94 test | Thickness of test piece | 1.6 mm | 1.6 mm | 1.6 mm | 1.6 mm | 1.6 mm | 1.6 mm | 1.6 mm | 1.6 mm | 1.6 mm |
| | | UL rating | V-0 | V-0 | V-0 | V-0 | V-0 | V-0 | V-0 | V-0 | V-0 |
| | | Drips | — | — | — | — | — | — | — | — | — |
| HDT | ISO 75-2 | ° C. | 56 | 57 | 57 | 55 | 56 | 56 | 56 | 58 | 59 |
| | 0.45 MPa | Retention (%) | 100 | 100 | 98 | 98 | 98 | 97 | 100 | 102 | 102 |

Ex.: Example

TABLE 3

| | Component | Unit | C. Ex. 1 | C. Ex. 2 | C. Ex. 3 | C. Ex. 4 | C. Ex. 5 | C. Ex. 6 |
|---|---|---|---|---|---|---|---|---|
| Composition | Component A | Type | PLA-1 | PLA-1 | PLA-1 | PLA-1 | PLA-1 | PLA-1 |
| | | Parts by weight | 100 | 100 | 100 | 100 | 100 | 100 |

TABLE 3-continued

|  |  |  |  |  |  |  |  |  |
|---|---|---|---|---|---|---|---|---|
|  | Component B | Type | HIPS | ABS | AS | HIPS | ABS | AS |
|  |  | Parts by weight | 15 | 15 | 15 | 20 | 20 | 20 |
|  | Component C | Type | — | — | — | — | — | — |
|  |  | Parts by weight | — | — | — | — | — | — |
| Flame retardancy | UL-94 test | Thickness of test piece | 1.6 mm | 1.6 mm | 1.6 mm | 1.6 mm | 1.6 mm | 1.6 mm |
|  |  | UL rating | V-2 | not V | not V | V-2 | not V | not V |
|  |  | Drips | X | — | — | X | — | — |
| HDT | ISO 75-2 | °C. | 56 | 57 | 57 | 56 | 57 | 58 |
|  | 0.45 MPa | Retention (%) | — | — | — | — | — | — |

|  | Component | Unit | C. Ex. 7 | C. Ex. 8 | C. Ex. 9 | C. Ex. 10 | C. Ex. 11 | C. Ex. 12 |
|---|---|---|---|---|---|---|---|---|
| Composition | Component A | Type | PLA-1 | PLA-1 | PLA-1 | PLA-1 | PLA-1 | PLA-1 |
|  |  | Parts by weight | 100 | 100 | 100 | 100 | 100 | 100 |
|  | Component B | Type | HIPS | ABS | AS | HIPS | ABS | AS |
|  |  | Parts by weight | 15 | 15 | 15 | 20 | 20 | 20 |
|  | Component C | Type | PX-200 | PX-200 | PX-200 | PX-200 | PX-200 | PX-200 |
|  |  | Parts by weight | 30 | 30 | 30 | 30 | 30 | 30 |
| Flame retardancy | UL-94 test | Thickness of test piece | 1.6 mm | 1.6 mm | 1.6 mm | 1.6 mm | 1.6 mm | 1.6 mm |
|  |  | UL rating | V-2 | V-2 | V-2 | V-2 | V-2 | V-2 |
|  |  | Drips | ○ | ○ | ○ | ○ | ○ | ○ |
| HDT | ISO 75-2 | °C. | 46 | 48 | 47 | 45 | 47 | 47 |
|  | 0.45 MPa | Retention (%) | 82 | 84 | 82 | 80 | 82 | 81 |

C. Ex.: Comparative Example

Examples 25 to 40 and Comparative Examples 13 to 20

The amounts (parts by weight) shown in Tables 4 to 6 of components shown in Tables 4 to 6 were mixed together by means of a tumbler, and the resulting mixtures were pelletized by means of a 15 mmφ double-screw extruder (KZW15 of Technovel Corporation). The obtained pellets were dried with a hot air drier at 80° C. for 24 hours. The dried pellets were molded by means of an injection molding machine (J75EIII of The Japan Steel Works, Ltd.). The evaluation results of the molded plates are shown in Tables 4 to 6.

TABLE 4

|  | Component | Unit | Ex. 25 | Ex. 26 | Ex. 27 | Ex. 28 | Ex. 29 | Ex. 30 | Ex. 31 | Ex. 32 |
|---|---|---|---|---|---|---|---|---|---|---|
| Composition | Component A | Type | PLA-2 | PLA-2 | PLA-2 | PLA-2 | PLA-2 | PLA-2 | PLA-2 | PLA-2 |
|  |  | Parts by weight | 100 | 100 | 100 | 100 | 100 | 100 | 100 | 100 |
|  | Component B | Type | PC-1 | PC-2 | PC-1 | PC-2 | PC-1 | PC-2 | PC-1 | PC-2 |
|  |  | Parts by weight | 15 | 15 | 20 | 20 | 15 | 15 | 20 | 20 |
|  | Component C | Type | FR-1 | FR-1 | FR-1 | FR-1 | FR-1 | FR-1 | FR-1 | FR-1 |
|  |  | Parts by weight | 20 | 20 | 20 | 20 | 30 | 30 | 30 | 30 |
| Flame retardancy | UL-94 test | Thickness of test piece | 1.6 mm | 1.6 mm | 1.6 mm | 1.6 mm | 1.6 mm | 1.6 mm | 1.6 mm | 1.6 mm |
|  |  | UL rating | V-0 | V-0 | V-0 | V-0 | V-0 | V-0 | V-0 | V-0 |
| HDT | ISO 75-2 | °C. | 57 | 59 | 58 | 58 | 58 | 59 | 58 | 57 |
|  | 0.45 MPa | Retention (%) | 102 | 105 | 104 | 104 | 104 | 105 | 104 | 102 |

Ex.: Example

TABLE 5

|  | Component | Unit | Ex. 33 | Ex. 34 | Ex. 35 | Ex. 36 | Ex. 37 | Ex. 38 | Ex. 39 | Ex. 40 |
|---|---|---|---|---|---|---|---|---|---|---|
| Composition | Component A | Type | PLA-2 | PLA-2 | PLA-2 | PLA-2 | PLA-2 | PLA-2 | PLA-2 | PLA-2 |
|  |  | Parts by weight | 100 | 100 | 100 | 100 | 100 | 100 | 100 | 100 |
|  | Component B | Type | PC-1 | PC-2 | PC-1 | PC-2 | PC-1 | PC-2 | PC-1 | PC-2 |
|  |  | Parts by weight | 20 | 20 | 20 | 20 | 20 | 20 | 20 | 20 |
|  | Component C | Type | FR-2 | FR-2 | FR-3 | FR-3 | FR-4 | FR-4 | FR-5 | FR-5 |
|  |  | Parts by weight | 30 | 30 | 30 | 30 | 30 | 30 | 30 | 30 |
| Flame retardancy | UL-94 test | Thickness of test piece | 1.6 mm | 1.6 mm | 1.6 mm | 1.6 mm | 1.6 mm | 1.6 mm | 1.6 mm | 1.6 mm |
|  |  | UL rating | V-0 | V-0 | V-0 | V-0 | V-0 | V-0 | V-0 | V-0 |
| HDT | ISO 75-2 | °C. | 57 | 58 | 56 | 57 | 55 | 55 | 57 | 56 |
|  | 0.45 MPa | Retention (%) | 102 | 104 | 100 | 102 | 98 | 98 | 102 | 100 |

Ex.: Example

TABLE 6

| Component | | Unit | C. Ex. 13 | C. Ex. 14 | C. Ex. 15 | C. Ex. 16 | C. Ex. 17 | C. Ex. 18 | C. Ex. 19 | C. Ex. 20 |
|---|---|---|---|---|---|---|---|---|---|---|
| Composition | Component A | Type | PLA-2 | PLA-2 | PLA-2 | PLA-2 | PLA-2 | PLA-2 | PLA-2 | PLA-2 |
| | | Parts by weight | 100 | 100 | 100 | 100 | 100 | 100 | 100 | 100 |
| | Component B | Type | PC-1 | PC-2 | PC-1 | PC-2 | PC-1 | PC-2 | PC-1 | PC-2 |
| | | Parts by weight | 15 | 15 | 20 | 20 | 15 | 15 | 20 | 20 |
| | Component C | Type | — | — | — | — | PX-200 | PX-200 | PX-200 | PX-200 |
| | | Parts by weight | — | — | — | — | 30 | 30 | 30 | 30 |
| Flame retardancy | UL-94 test | Thickness of test piece | 1.6 mm | 1.6 mm | 1.6 mm | 1.6 mm | 1.6 mm | 1.6 mm | 1.6 mm | 1.6 mm |
| | | UL rating | not V | not V | not V | not V | V-2 | V-2 | V-2 | V-2 |
| HDT | ISO 75-2 | °C. | 56 | 56 | 56 | 56 | 47 | 48 | 47 | 48 |
| | 0.45 MPa | Retention (%) | — | — | — | — | 84 | 86 | 84 | 86 |

C. Ex.: Comparative Example

EFFECT OF THE INVENTION

The flame retardant resin composition of the present invention and a molded article formed therefrom have the following advantages over conventional resin compositions obtained from plant-derived raw materials.
(i) A resin composition having high flame retardancy is obtained from a plant-derived raw material without using a halogen-containing flame retardant substantially.
(ii) Since an organic phosphorus compound as a flame retardant has an excellent flame retarding effect for a resin obtained from a plant-derived raw material, V-2 rating, particularly preferably V-0 rating is achieved even with a relatively small amount thereof.
(iii) Since a resin obtained from a plant-derived raw material rarely thermally deteriorates at the time of molding the resin obtained from a plant-derived raw material or using a molded article thereof due to the structure and characteristic properties of the organic phosphorus compound used as a flame retardant, a resin composition having excellent heat resistance is obtained. Therefore, a composition having good balance among flame retardancy, mechanical strength and heat resistance is obtained.
(iv) Since the organic phosphorus compound as a flame retardant is achromatic and compatible with a resin obtained from a plant-derived raw material, a molded article having excellent transparency can be obtained.

Industrial Applicability

The flame retardant resin composition of the present invention is useful as a material for forming various molded articles such as home electric appliance parts, electric and electronic parts, auto parts, mechanical and machine and mechanism parts, and cosmetic containers.

The invention claimed is:

1. A flame retardant resin composition comprising:
(A) 100 parts by weight of a polylactic acid and/or a lactic acid copolymer (component A);
(B) 1 to 100 parts by weight of a styrene-based resin and/or a polycarbonate resin (component B); and
(C) 10 to 70 parts by weight of an organic phosphorus compound represented by the following formula (1),

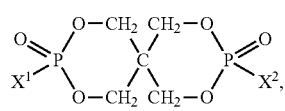

(1)

wherein $X^1$ and $X^2$ are the same or different and each is an aromatic substituted alkyl group represented by the following formula (2), $$ALAr)_n \quad (2),$$

wherein AL is a branched or linear aliphatic hydrocarbon group having 1 to 5 carbon atoms, Ar is a phenyl group, a naphthyl group or an anthryl group all of which may have a substituent, n is an integer of 1 to 3, and Ar can be bonded to any carbon atom contained in the AL.

2. The flame retardant resin composition according to claim 1, wherein the organic phosphorus compound (component C) is at least one compound selected from the group consisting of
(i) an organic phosphorus compound represented by the following formula (3),

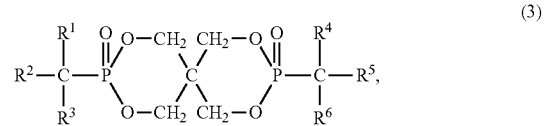

(3)

wherein $R^2$ and $R^5$ may be the same or different and each is a phenyl group, a naphthyl group or an anthryl group all of which may have a substituent, $R^1$, $R^3$, $R^4$ and $R^6$ may be the same or different and each is a substituent selected from the group consisting of a hydrogen atom, a branched or linear alkyl group having 1 to 4 carbon atoms, a phenyl group which may have a substituent, a naphthyl group which may have a substituent and an anthryl group which may have a substituent, and
(ii) an organic phosphorus compound represented by the following formula (4),

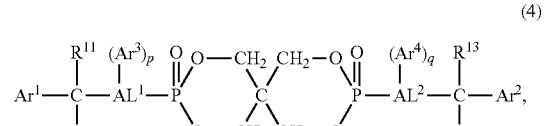

(4)

wherein $Ar^1$ and $Ar^2$ may be the same or different and each is a phenyl group, a naphthyl group or an anthryl group and may have a substituent in the aromatic ring, $R^{11}$, $R^{12}$, $R^{13}$ and $R^{14}$ may be the same or different and each is a hydrogen atom, an aliphatic hydrocarbon group having 1 to 3 carbon atoms, a phenyl group, a naphthyl group or an anthryl group and may have a substituent in the aromatic ring, $AL^1$ and $AL^2$ may be the same or different and each is a branched or linear aliphatic hydrocarbon group having 1 to 4 carbon atoms, $Ar^3$ and $Ar^4$ may be the same or different and each is a phenyl group, a naphthyl group or an anthryl group and may have a substituent in the aromatic ring, p and q are each an integer of 0 to 3, $Ar^3$ can be bonded to any carbon atom in $AL^1$ and $Ar^4$ can be bonded to any carbon atom in $AL^2$.

3. The flame retardant resin composition according to claim 1, wherein the organic phosphorus compound (component C) is represented by the following formula (5),

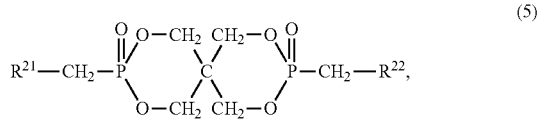
(5)

wherein $R^{21}$ and $R^{22}$ are the same or different and each is a phenyl group, a naphthyl group or an anthryl group and may have a substituent in the aromatic ring.

4. The flame retardant resin composition according to claim 1, wherein the organic phosphorus compound (component C) is a compound represented by the following formula (1-a),

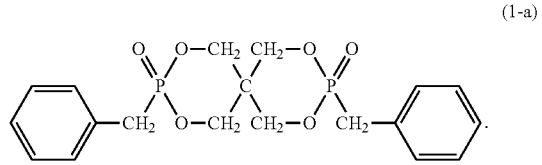
(1-a)

5. The flame retardant resin composition according to claim 1, wherein the organic phosphorus compound (component C) is represented by the following formula (6),

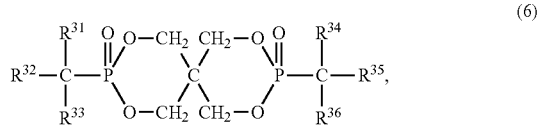
(6)

wherein $R^{31}$ and $R^{34}$ may be the same or different and each is a hydrogen atom or an aliphatic hydrocarbon group having 1 to 3 carbon atoms, $R^{33}$ and $R^{36}$ may be the same or different and each is an aliphatic hydrocarbon group having 1 to 4 carbon atoms, $R^{32}$ and $R^{35}$ may be the same or different and each is a phenyl group, a naphthyl group or an anthryl group and may have a substituent in the aromatic ring.

6. The flame retardant resin composition according to claim 1, wherein the organic phosphorus compound (component C) is a compound represented by the following formula (1-b),

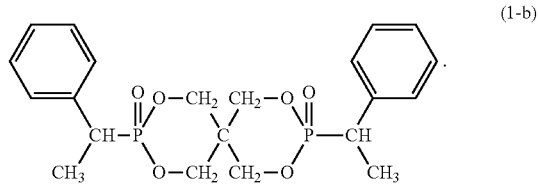 [SMILES: CC(c1ccccc1)P1(=O)OCC2(CO1)COP(=O)(C(C)c1ccccc1)OC2]
(1-b)

7. The flame retardant resin composition according to claim 1, wherein the organic phosphorus compound (component C) is represented by the following formula (7),

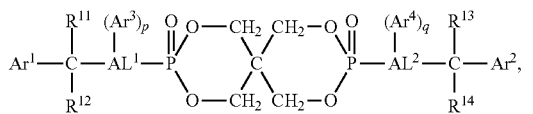
(7)

wherein $Ar^1$ and $Ar^2$ may be the same or different and each is a phenyl group, a naphthyl group or an anthryl group and may have a substituent in the aromatic ring, $R^{11}$, $R^{12}$, $R^{13}$ and $R^{14}$ may be the same or different and each is a hydrogen atom, an aliphatic hydrocarbon group having 1 to 3 carbon atoms, a phenyl group, a naphthyl group or an anthryl group and may have a substituent in the aromatic ring, $AL^1$ and $AL^2$ may be the same or different and each is a branched or linear aliphatic hydrocarbon group having 1 to 4 carbon atoms, $Ar^3$ and $Ar^4$ may be the same or different and each is a phenyl group, a naphthyl group or an anthryl group and may have a substituent in the aromatic ring, p and q are each an integer of 0 to 3, $Ar^3$ can be bonded to any carbon atom in $AL^1$ and $Ar^4$ can be bonded to any carbon atom in $AL^2$.

8. The flame retardant resin composition according to claim 1, wherein the organic phosphorus compound (component C) is a compound represented by the following formula (1-c),

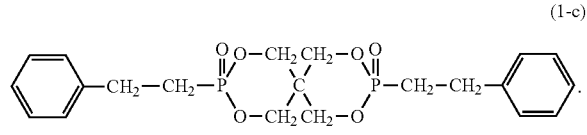
(1-c)

9. The flame retardant resin composition according to claim 1, wherein the organic phosphorus compound (component C) is represented by the following formula (8),

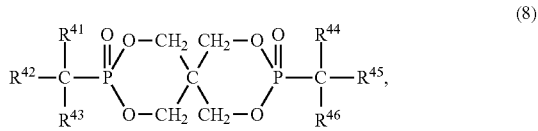
(8)

wherein $R^{41}$ and $R^{44}$ may be the same or different and each is a hydrogen atom, an aliphatic hydrocarbon group having 1 to 4 carbon atoms, a phenyl group, a naphthyl group or an anthryl group and may have a substituent in the aromatic ring, $R^{42}$, $R^{43}$, $R^{45}$ and $R^{46}$ may be the same or different and each is a phenyl group, a naphthyl group or an anthryl group and may have a substituent in the aromatic ring.

10. The flame retardant resin composition according to claim 1, wherein the organic phosphorus compound (component C) is a compound represented by the following formula (1-d),

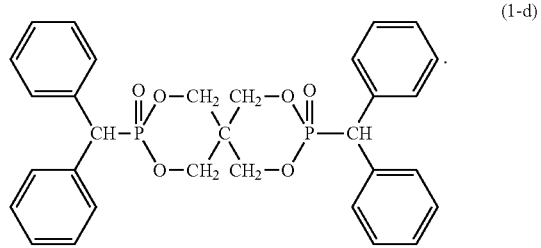 [SMILES: O=P1(C(c2ccccc2)c2ccccc2)OCC2(CO1)COP(=O)(C(c1ccccc1)c1ccccc1)OC2]

11. The flame retardant resin composition according to claim 1, wherein an acid value of the organic phosphorus compound (component C) is not more than 0.7 mgKOH/g.

12. The flame retardant resin composition according to claim 1 which achieves at least a V-2 rating according to the UL-94 flame retardancy standard.

13. The flame retardant resin composition according to claim 1, wherein the styrene-based resin (component B) has an MVR value at 200° C. under a load of 5 kg of 1 to 100 cm$^3$/10 min.

14. The flame retardant resin composition according to claim 1, wherein the styrene-based resin (component B) has an MVR value at 220° C. under a load of 10 kg of 1 to 100 cm$^3$/10 min.

15. The flame retardant resin composition according to claim 1, wherein the polycarbonate resin (component B) has an MVR value at 300° C. under a load of 1.2 kg of 0.1 to 80 cm$^3$/10 min.

16. The flame retardant resin composition according to claim 1, wherein the polycarbonate resin (component B) has a content of an OH group existent at a terminal of not more than 100 eq/ton.

17. The flame retardant resin composition according to claim 1 which has an HDT retention measured under a load of 0.45 MPa of not less than 95%.

18. A molded article obtained from the flame retardant resin composition of claim 1.

* * * * *